United States Patent [19]

Asinger et al.

[11] 3,966,752

[45] June 29, 1976

[54] RESOLUTION OF D,L-PROTECTED-PENICILLAMINE

[75] Inventors: Friedrich Asinger, Aachen; Heribert Offermanns, Grossauheim; Karl-Heinz Gluzek, Alpen; Walter vonBebenburg, Buchschlag, all of Germany

[73] Assignee: Deutsche Gold- und Silber-Scheideanstalt vormals Roessler, Germany

[22] Filed: Nov. 4, 1974

[21] Appl. No.: 520,899

Related U.S. Application Data

[63] Continuation-in-part of Ser. No. 276,530, July 31, 1972, abandoned, and a continuation-in-part of Ser. No. 419,473, Nov. 27, 1973, abandoned.

[52] U.S. Cl. .................... 260/306.7 C; 260/534 S
[51] Int. Cl.² .................................. C07D 277/06
[58] Field of Search .............. 260/570.6, 306.7 C, 260/534 S

[56] References Cited
UNITED STATES PATENTS

| | | |
|---|---|---|
| 1,867,274 | 7/1932 | Manske ........................ 260/570.6 |
| 2,450,784 | 10/1948 | Duffin et al. .................. 260/306.7 |

OTHER PUBLICATIONS

Stewart, *Stereo Chemistry*, Langmans, Green & Co., London, 1919, pp. 40–42.

*Primary Examiner*—R. J. Gallagher
*Attorney, Agent, or Firm*—Cushman, Darby & Cushman

[57] ABSTRACT

The D-form of an optically active protected penicillamine is prepared by treating a solution of D,L protected penicillamine of the formula:

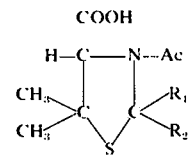

wherein Ac is formyl, and $R_1$ and $R_2$ are both methyl or are joined together to form the pentamethylene group.

27 Claims, No Drawings

RESOLUTION OF D,L-PROTECTED-PENICILLAMINE

The present application is a continuation-in-part of application Ser. No. 276,530, filed July 31, 1972 and now abandoned and application Ser. No. 419,473, filed Nov. 27, 1973 and now abandoned, the entire disclosures of which are hereby incorporated by reference and relied upon.

It is not possible to predict the ability of an acid to resolve a racemate of an optically active amine (or of an amine to resolve the racemate of an optically active acid). Thus, Eliel "Stereochemistry of carbon Compounds"difficulty soluble 1962) pgs. 49–50 points out that this can be only done by trial and error. As an illustration Eliel points out that while it might be thought that mandelic acid (alpha-hydroxy-beta-phenylacetic acid) and atrolactic acid (alpha-hydroxy-alpha-methyl-beta-phenylacetic acid) might be considered similar, nevertheless, ephedrine can resolve mandelic acid but not atrolactic acid.

Likewise Greenstein and Winitz "Chemistry of the Amino Acids" Vol. 1, pgs. 716–718 points out that the resolution procedure is rather empirical, and that none of the conditions necessary for a successful resolution can be predicted, a priori, and the resolution of each individual racemate constitutes a separate experimental problem.

The aminoacid D-penicillamine is known to be an important medicine for the treatment of Morbus Wilson, defective schizophrenia, scleroderma, cystinuria and chronic agressive hepatitis as well as basic therapy of primary chronic polyarthritis. D-penicillamine is also useful as an antidote for heavy metal intoxications.

Therapeutic uses are only found for D-penicillamine since the L-isomer is much more toxic.

It is known to recover D-penicillamine in an expensive, hydrolytic process from penicillin which explains the high price of this aminoacid in consideration of the high value of the starting material. This hinders the wide medicinal use of D-penicillamine, especially as a basic therapeutic for long lasting treatment of primary chronic polyarthritis. For this reason a total synthesis of D-penicillamine is of especial significance.

It is also known, however, to produce D,L-penicillamine synthetically and to recover the D-penicillamine by splitting the racemate. As optically active bases for this purpose there have been used d-pseudoephedrine and 1-ephedrine (see "The Chemistry of Penicilline" (1949) Princeton University Press; British Pat. No. 585,413 and corresponding Duffin U.S. Pat. No. 2,450,784 and Belgian Pat. No. 738,520).

For the racemate splitting, the D,L-penicillamine must be converted into suitable derivatives, that is protective groups must be introduced into the penicillamine molecule, as is customary in the resolution of amino acids. Suitable derivatives for the resolution for example are the N-acylated products of D,L-penicillamine or of S-benzyl-D,L-penicillamine as well as the acylation product of the reaction product of D,L-penicillamine with carbonyl compounds.

These processes for the resolution of D,L-penicillamine, however, are only slightly satisfactory since in the reaction of the D,L-penicillamine derivatives with the above named splitting bases the undesired salt of the L-penicillamine derivative and the optically active base precipitates. It is known, however, that in principle the antipode crystallizing out of the reaction mixture has the higher purity (H. D. Jakubke and H. Jeschkeit, "Aminosaeuren, Peptide, Proteine," Akademie-Verlag, Berlin, 1969, as well as L. F. Fieser and M. Fieser, "Lehrbuch der Organischen Chemie", Verlag Chemie, Weinheim, 1957).

It has now been found that it is especially advantageous to use 1-norephedrine (phenylpropanolamine) of the formula:

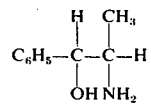

for the recovery of D-penicillamine from D,L-penicillamine. The resolution of D,L-penicillamine proceeds with the help of this optically active base with high yields and the D-penicillamine is obtained in high purity since the desired salt of the D-acid and the L-base is difficultly soluble and precipitates.

As in the known process for resolution also in the process of the present invention the D,L-penicillamine must first be converted into a suitable derivative for the racemate splitting before the reaction with the 1-norephedrine can take place, i.e., one or both hydrogen atoms of the amino group must first be protected. For this purpose there can be used any of the known methods, such as those described in "Chemistry of the Aminoacids", J. P. Greenstein and M. Winitz, J. Wiley and Sons, Inc., New York 1961, as well as in Houben Weyl, 1958, Vol. 11, part 2, Georg Thiem Verlag. Such protection can be obtained for example if D,L-penicillamine is converted, in known manner into a thiazolidine-4-carboxylic acid of the formula:

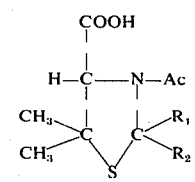

in which $R_1$ and $R_2$ are both methyl or are joined together to form the pentamethylene group, and Ac is the formyl group:

There is preferably used N-formyl-2,2,5,5-tetramethyl-thiazolidine-4-carboxylic acid (N-formyl-isopropylidene-D,L-penicillamine). these thiazolidine-4-carboxylic acids can be made in a simple manner from D,L-penicillamine and the corresponding carbonyl compounds (The Chemistry of Penicilline (1949), Princeton University Presss). The conversion into the N-acyl compounds as well as the compounds with protected mercapto groups is described in the same literature.

Also, there can be used D,L-3-formyl-2,2-pentamethylene-5,5-dimethyl-thiazolidine-4-carboxylic acid.

As solvents for the separation of the racemate there can be used water or more preferably organic solvents such as alcohols, halogenated aliphatic hydrocarbon, dioxane, ketones, esters, aromatic hydrocarbons, etc. There are preferably used benzene, toluene, isopropanol, dioxane and lower carboxylic acid esters, e.g., ethyl acetate.

Specific examples of additionally suitable solvents include methanol, ethanol, butanol, isooctyl alcohol, isodecyl alcohol, dodecyl alcohol, chloroform, carbon tetrachloride, dichloroethylene, 1,1,2,2-tetrachloroethane, dibromoethylene, acetone, methyl ethyl ketone, methyl butyl ketone, diethyl ketone, ethyl formate, ethyl propionate, methyl formate, ethyl formate, ethyl propionate, ethyl butyrate, propyl acetate, ethyl propionate.

In the carrying out of the process of the invention, there is first provided that the D,L-penicillamine is converted in known way to a suitable derivative (protected D,L-penicillamine) and this is dissolved in water or preferably in an organic solvent or mixture of organic solvents such as those set forth above and this solution, in a given case with heating mixed with 1-norephedrine, in a given case dissolved in an organic solvent such as any of those set forth above. Frequently immediately or, under some conditions, only after long standing, in a given case at low temperatures and after inoculation the more difficultly soluble salt of the D-penicillamine derivative and 1-norephedrine precipitates out while the diastereoisomeric salt, the optical antipode or the racemate mixture or mixtures thereof remains in the mother liquer. The difficultly soluble salt can be converted into the mineral acid salt of D-penicillamine in known manner, for example by treatment with dilute mineral acid, e.g., hydrochloric acid, hydrobromic acid, sulfuric acid, nitric acid. The free D-penicillamine can likewise be set free in known manner from the mineral acid salt, for example, by treatment with a base, e.g., sodium hydroxide, potassium hydroxide, barium hydroxide, calcium hydroxide, sodium carbonate, potassium carbonate, amines, e.g., triethyl amine, tripropylamine, tributylamine, etc.

The process can be carried out in reverse and the solution of the 1-norephedrine mixed with the derivative of the racemic penicillamine which preferably is dissolved in an organic solvent such as those set forth above, for example.

The process of the invention is advantageously carried out using 0.1 to 3 moles, preferably 0.5 to 1.1 moles of 1-norephedrine per mole of racemate. In all ranges the more difficultly soluble salt of the D-penicillamine derivative and 1-norephedrine precipitates. This precipitation is nearly quantitative by employing approximately stoichiometric quantities of reactants. Using less than 0.5 mole of 1-norephedrine there remains in the mother liquer the racemate and optical antipode; using per mole of racemate between 0.5 and <1 mole of 1-ephedrine the mother liquer still contains besides the optical antipodes diastereomer salt. If there is added per mole of racemate more than 1 mole of the optically active 1-norephedrine there is still contained in the mother liquer in addition to the diastereomeric salt some 1-norephedrine.

The salt of the penicillamine derivative and 1-norephedrine accumulating in the reaction can be recovered in pure form in known manner because of its very favorable solubility relation, for example, by filtration, evaporation of the mother liquer and purification by recrystallization.

In each case there precipitates first in the racemate splitting the more difficultly soluble salt of the D-penicillamine derivative and 1-norephedrine while the other diastereomer remains in solution. This was completely surprising since in the use of both D-pseudoephedrine and 1-ephedrine the salt of the L-penicillamine derivative and the splitting base is more difficultly soluble.

The splitting of the more difficultly soluble salt likewise occurs in known manner through treatment with preferably aqueous mineral acids, for example, dilute hydrochloric acid (or any of the other mineral acids mentioned above), whereby first the optically active base (1-norephedrine) is recovered in the form of the mineral acid salt and the D-penicillamine derivative is obtained.

The splittig of the D-penicillamine derivative likewise takes place in known manner by splitting off the protective group, for example debenzylation or acid hydrolysis.

In an analogous manner L-penicillamine can be recovered from the mother liquer of the splitting of the racemate. It is especially advantageous, however, to racemize the L-penicillamine derivatives in known manner, in a given case recovered through mineral acid splitting of its salt with the optically active 1-norephedrine, whereby it is possible to recycle the therapeutically nonusable L-penicillamine after racemisation.

Unless otherwise indicated, all parts and percentages are by weight.

EXAMPLE 1

In a 50 liter glass reaction vessel provided with stirrer, reflux condenser, dropping funnel, gas inlet tube and bottom outlet valve there were dissolved 3.26 kilograms (15 moles) of N-formyl-isopropylidene, D,L-penicillamine in 20 liters of ethyl acetate with heating to 50°C. (The N-formyl-isopropylidene-D,L-penicillamine was obtained by reaction of 3 kilograms of D,L-penicillamine hydrochloride (16 moles) with 2,8 kilograms of acetone (50 moles) and subsequently formylation with a mixture of formic acid and acetic anhydride with simultaneous neutralization with sodium acetate). To this solution of N-formyl-isopropylidene-D,L-penicillamine there were added with stirring and further heating 3.28 kilograms (1.05 × 15 moles) of 1-norephedrine dissolved in 7 liters of ethyl acetate whereby there was observed an increase in temperature of 5°C. After a few minutes there precipitated the adduct (1) of N-formyl-isopropylidene-D-penicillamine and 1-norephedrine. Stirring was continued for another half hour with heating at reflux. After cooling the product was filtered off with strong suction, the residue on the filter washed with about 3 liters of ethyl acetate and dried under reduced pressure at about 50°C. There were obtained 2.75 kilograms (equal to 98%) of adduct (1) having a melting point of 200°–204°C.; $[\alpha]_D^{20}$ + 33°.

From the mother liquer there were obtained after evaporation to dryness crude adduct (2) of N-formyl-isopropylidene-L-penicillamine and 1-norephedrine from which the pure adduct having a melting point of 116°C. and $[\alpha]_D^{20}$ −74.6° could be recovered by recrystallization from isopropyl alcohol.

2.75 kilograms of adduct (1) were treated at 25°C. successively with 10 liters of distilled water and 1 liter of concentrated hydrochloric acid. After stirring for one hour the product was filtered with strong suction, washed with 2 liters of distilled water and the residue dried at 50°C. under reduced pressure. There were obtained 1.49 kilograms (equal to 92%) of N-formyl-isopropylidene-D-penicillamine having a melting point of 183°–184°C. and $[\alpha]_D^{20}$ + 53°. From the mother liquer there were obtained after evaporation to dryness and recrystallization from isopropyl alcohol 1.19 kilograms of 1-norephedrine. HCl melting at 172°–174°C.

1.49 kilograms of N-formyl-isopropylidene-D-penicillamine were added to 9.0 liters of 15% aqueous hydrochloric acid which was heated to 70°C. With distillation of the acetone set free heating was continued for 2 hours at the same temperature. After evaporating to dryness in a 50 liter rotatory evaporator there were obtained 1.08 kilograms of crude D-penicillamine. HCl.

1.08 kilograms of D-penicillamine.HCl were dissolved in 8.7 liters of 96% ethyl alcohol and treated with 0.59 kilograms (5.82 mole) of triethylamine whereby the free D-penicillamine precipitated. After filtering with suction, subsequent washing with 06% ethyl alcohol and drying under reduced pressure at 50°C. there were obtained 0.78 kilograms of D-penicillamine having a melting point of 212°–214°C. and $[\alpha]_D^{20} - 62.8°$.

The working up of crude adduct (2) takes place in a manner analogous to the working up of adduct (1). There were obtained 1.3 kilograms of N-formyl-isopropylidene-1-penicillamine having a melting point of 182°–184°C. and $[\alpha]_D^{20} - 53°$.

1.3 kilograms of N-formyl-isopropylidene-L-penicillamine were dissolved in 4.5 liters of toluene and treated with 30 ml. of acetic anhydride. This mixture was heated for 2 hours under reflux. After cooling to room temperature the pure N-formyl-isopropylidene-D,L-penicillamine crystallized out. There were obtained 1.25 kilograms of N-formyl-isopropylidene-D,L-penicillamine having a melting point of 140°–142°C. and $[\alpha]_D^{20} = 0°$.

EXAMPLE 2

In a 1 liter plural necked flask provided with stirrer, dropping funnel, gas inlet tube and reflux condenser there were dissolved 43.5 grams (0.2 mole) of N-formyl-isopropylidene-D,L-penicillamine in 300 ml of ethyl acetate with heating to 50°C. To this solution there was added in portions within 5 minutes 16.7 grams (0.11 mole) of 1-norephedrine and the mixture heated for 30 minutes under reflux. After cooling to room temperature the product was filtered off with strong suction, washed with 150 ml. of ethyl acetate and dried under reduced pressure at 50°C. There were obtained 33.9 grams (equal to 92%) N-formyl-isopropylidene-D-penicillamine-1-norephedrine, adduct (1) having a melting point of 202°–204°C. and $[\alpha]_D^{20} + 31°$. The splitting of the adduct took place in the manner described in Example 1. There were obtained 10 grams of D-penicillamine having a melting point of 212°–214°C. and $[\alpha]_D^{20} - 62.7°$.

EXAMPLE 3

The procedure described in Example 2 was followed except that there was used isopropyl alcohol as the solvent. There were obtained 33.1 grams (90%) of adduct (1) from which there were obtained by splitting 9.7 grams of D-penicillamine melting at 211°–213°C. and $[\alpha]_D^{20} - 62.7°$.

EXAMPLE 4

The procedure of Example 2 was followed except that there was used toluene as the solvent. There were obtained 32 grams (87%) of adduct (1) having a melting point of 201°–202°C. and $[\alpha]_D^{20} + 31.8°$.

EXAMPLE 5

The procedure of Example 1 was followed, however, using 21.8 grams (0.1 mole) of N-formyl-isopropylidene-D,L-penicillamine and 15.1 grams (0.1 mole) of 1-norephedrine and using 150 ml of acetone as the solvent. There were obtained 28.5 grams (equal to 78%) of the adduct (1) having a melting point of 200°–204°C. and $[\alpha]_D^{20} + 31°$.

EXAMPLE 6

The procedure described in Example 5 was employed using, however, dioxane as the solvent. There were obtained 28 grams (equal to 75%) of adduct (1) having a melting point of 195°–196°C. and $[\alpha]_D^{20} + 30.7°$.

EXAMPLE 7

The procedure of Example 5 was followed except there was used benzene as the solvent. There were obtained 33 grams (equal to 90%) of adduct (1) melting at 197°–201°C. and $[\alpha]_D^{20} + 31°$.

EXAMPLE 8

The procedure of Example 5 was followed except that there was used carbon tetrachloride as the solvent. There were obtained 34 grams (equal to 93%) of adduct (1) melting at 200°–201°C. and $[\alpha]_D^{20} + 35°$.

It has also been found that it is especially advantageous to add the 1-norephedrine as a salt rather than as the free base as set forth in the parent application and corresponding German application P 21 38 122 in the recovery of D-penicillamine from D,L-penicillamine.

L-norephedrine generally is produced in the form of its salts. When these salts are added directly in the use of norephedrine for the recovery of D-penicillamine there is saved the production of the free base of norephedrine.

As salts of 1-norephedrine there are chiefly employed salts of organic acids preferably with sulfonic acids and even more preferably with carboxylic acids. As sulfonic acids there can be used for example aliphatic sulfonic acids, e.g., alkane sulfonic acids such as methane sulfonic acid, methane trisulfonic acid, propan-2-sulfonic acid, ethane sulfonic acid, propan-1-sulfonic acid, butan-1-sulfonic acid, decane-1-sulfonic acid, octadecan-1-sulfonic acid; or aromatic sulfonic acids, e.g., aryl sulfonic acids such as p-toluene sulfonic, beta-naphthalene sulfonic acid, alpha-naphthalene sulfonic acid and especially benzene sulfonic acid. As carboxylic acids there can be used saturated or unsaturated aliphatic mono or poly carboxylic acids, in a given case substituted by —OH, H$_2$N—, NHR—,

—OR, —SH, —SR or halogen where R for example is an alkyl group. The preferred acids are aliphatic acids having 1 to 6 carbon atoms, especially alkanoic acids having 1 to 6 carbon atoms, most preferably having 1 to 3 carbon atoms. There are also useful araliphatic carboxylic acids, especially phenylalkanoic acids or aromatic carboxylic acids, or heteroaromatic carboxylic acids (i.e., heterocyclic carboxylic acids). Suitable carboxylic acids include isobutyric acid, n-valeric acid, trimethyl acetic acid, lactic acid, oxalic acid, sebacic acid, maleic acid, adipic acid, malonic acid, tartaric acid, succinic acid, fumaric acid, tricarballylic acid, citric acid, crotonic acid, 6-hydroxy hexanoic acid, chloroacetic acid, p-chlorobenzoic acid, bromoacetic acid, fluoroacetic acid, butyric acid, caproic acid, alpha naphthoic acid, beta-chloropropionic acid, methoxyacetic acid, thioglycolic acid, methylmercaptoacetic acid, beta mercaptopropionic acid, acetic acid, propionic acid, formic acid, octanoic acid, phenyl acetic acid, phenyl propionic acid, phenoxyacetic acid, 2,4-dichlorophenoxy acetic acid, 2,4,5-trichlorophenoxyacetic acid, mandelic acid, cinnamic acid, toluic acid, phthalic acid, isophthalic acid, terephthalic acid, 4-chlorophthalic acid, benzoic acid, salicylic acid, thiophene-2-carboxylic acid, thiophene-3-carboxylic acid, thiazole-4-carboxylic acid, furan-2-carboxylic acid, 2-pyridinecarboxylic acid (picolinic acid), 3-pyridinecarboxylic acid (nicotinic acid), 4-pyridinecarboxylic acid (isonicotinic acid), 3-indoleacetic acid, 2,3-pyridinedicarboxylic acid.

Less preferably there are employed salts of inorganic acids such as sulfuric acid, hydrochloric acid, hydrobromic acid nitric acid, phosphoric acid.

The salts of 1-norephedrine can be used in the same manner, under the same conditions and in corresponding amounts (i.e., on a molar basis except that with polybasic acids the salt contains 1 mole of norephedrine for each acid group as the free base of 1-norephedrine). The use of the salt is especially recommended for carrying out the resolution of D,L-penicillamine if it is present as an N-acyl (e.g., N-acyl-2,2,5,5-tetramethyl-thiazolidine-4-carboxylic acid) preferably as an N-formyl derivative, namely as N-formyl-2,2,5,5-tetramethyl-thiazolidine-4-carboxylic acid (N-formyl isopropylidene-D,L-penicillamine) or N-formyl-2,2-pentamethylene-5,5-dimethyl-thiazolidine-4-carboxylic acid.

In the following examples the rotatory power of the materials is always given as specific rotation $[\alpha]_D^{20}$ in degrees × cm$^3$/decimeter × grams. Percents are always weight percents.

EXAMPLE 9

21.7 grams (0.1 mole) of N-formyl-isopropylidene-D,L-penicillamine were dissolved in 80 ml of n-butyl acetate at 60° to 70°C. The solution was treated with stirring with 11.7 grams (0.06 mole) of 1-norephedrine-acetate and then held for 30 minutes at 80° to 85°C. First there was formed a clear solution; several minutes later there separated the adduct of N-formyl isopropylidene-D-penicillamine and 1-norephedrine. After slow cooling to room temperature it was filtered with suction. The adduct obtained was washed with 20 ml of n-butyl acetate and then dried under reduced pressure. It had a specific rotation of +34° and a melting point of 200° to 203°C. The yield was 11.5 grams, corresponding to 63% based on the N-formyl-isopropylidene-D,L-penicillamine employed.

11 grams of the adduct of N-formyl-isopropylidene-D,L-penicillamine and 1-norephedrine were suspended in 40 ml of water. The mixture was adjusted to a pH of 1 with concentrated hydrochloric acid at room temperature. In the course of the next 15 minutes there separated N-formyl-isopropylidene-D-penicillamine. It was filtered off under suction, washed with 10 ml of water and dried at reduced pressure. The N-formyl-isopropylidene-D-penicillamine had a specific rotation of +52° and a melting point of 182° to 183°C. The yield amounted to 5.8 grams, corresponding to 90% based on the adduct employed.

EXAMPLE 10

The procedure of Example 9 was employed but there were reacted 21.7 grams (0.1 mole) of N-formyl-isopropylidene-D,L-penicillamine with 21 grams (0.1 mole) of 1-norephedrine-acetate in 100 ml of ethyl acetate. The adduct recovered had a specific rotation of +32° and a melting point of 199° to 201°C. The yield amounted to 15 grams, corresponding to 82%.

EXAMPLE 11

The procedure of Example 9 was followed but there were reacted 43.6 grams (0.2 mole) of N-formyl-isopropylidene-D,L-penicillamine with 24.8 grams (0.11 mole) of 1-norephedrine propionate in 180 ml of toluene. The adduct obtained of N-formyl-isopropylidene-D-penicillamine and 1-norephedrine had a specific rotation of +30° and a melting point of 201°–204°C. The yield was 24 grams, corresponding to 65%.

EXAMPLE 12

The procedure of Example 9 was followed but there were reacted 21.7 grams (0.1 mole) of N-formyl-isopropylidene-D,L-penicillamine with 11.5 grams (0.02 mole) of 1-norephedrinemaleate in 80 ml of ethyl acetate. The adduct of N-formyl-isopropylidene-D-penicillamine and 1-norephedrine obtained had a specific rotation of +27° and a melting point of 199° to 201°C. The yield was 9.4 grams, corresponding to 51%.

EXAMPLE 13

The procedure of Example 9 was followed but there were reacted 43.5 grams (0.2 mole) of N-formyl-isopropylidene-D,L-penicillamine with 30 grams (0.11 mole) of 1-norephedrinebenzoate. The adduct obtained had a specific rotation of +30° and a melting point of 200° to 203°C. The yield was 24 grams, corresponding to 65%.

EXAMPLE 14

The procedure of Example 9 was followed but there were reacted 21.7 grams (0.1 mole) of N-formyl-isopropylidene-D,L-penicillamine with 10.8 grams (0.06 mole) of 1-norephedrineformate. The adduct obtained had a specific rotation of +32° and a melting point of 198° to 201°C. The yield was 11 grams, corresponding to 60%.

EXAMPLE 15

The procedure of Example 9 was followed but there were reacted 21.7 grams (0.1 mole) of N-formyl-isopropylidene-D,L-penicillamine with 16.5 grams (0.06 mole) 1-norephedrine-3-phenylpropionate. The adduct obtained had a specific rotation of +32° and a melting point of 198° to 202°C. The yield was 11.5 grams, corresponding to 62%.

EXAMPLE 16

The procedure of Example 9 was followed but there were reacted 21.7 grams (0.1 mole) of N-formyl-isopropylidene-D,L-penicillamine with 33 grams (0.11 mole) of 1-norephedrinebenzenesulfonate. The adduct obtained had a specific rotation of +31° and a melting point of 197° to 199°C. The yield was 14 grams, corresponding to 76%.

EXAMPLE 17

The procedure of Example 9 was followed but there were reacted 21.7 grams (0.1 mole) of N-formyl-isopropylidene-D,L-penicillamine with 21.5 grams (0.03 mole) of 1-norephedrine citrate. The adduct obtained had a specific rotation of 30° and a melting point of 198° to 200°C. The yield was 13 grams, corresponding to 70%.

EXAMPLE 18

The procedure of Example 9 was followed but there were reacted 25.7 grams (0.1 mole) of D,L-N-formyl-2,2-pentamethylene-5,5-dimethyl-thiazolidine-4-carboxylic acid with 10.8 grams (0.06 mole) of 1-norephedrine-formate. The adduct of D-n-formyl-2,2-pentamethylene-5,5-dimethyl thiazolidine-4-carboxylic acid and 1-norephedrine obtained had a specific rotation of +25° and a melting point of 190° to 191°C. The yield was 16.5 grams, corresponding to 90%.

EXAMPLE 19

The procedure of Example 9 was followed but there were reacted 25.7 grams (0.1 mole) of D,L-N-formyl-2,2-pentamethylene-5,5-dimethyl thiazolidine-4-carboxylic acid with 16.5 grams (0.06 mole) of 1-norephedrine benzenesulfonate. The adduct obtained had a specific rotation of +24° and a melting point of 189° to 191°C. The yield was 14.5 grams, corresponding to 71%.

EXAMPLE 20

The procedure of Example 1 was followed except that there were used 51.4 grams (0.2 mole) of D,L-3-formyl-2,2-pentamethylene-5,5-dimethyl-thiazolidine-4-carboxylic acid and 30.2 grams (0.2 mole) of 1-norephedrine as starting materials. The recovered salt of D-3-formyl-2,2-pentamethylene-5,5-dimethyl-thiazolidine-4-carboxylic acid and 1-norephedrine had a specific rotation of +26° and a melting point of 189°–191°C. The yield was 33 grams, corresponding to 81%.

EXAMPLE 21

The procedure described in Example 1 was employed except that there were used 51.4 grams (0.2 mole) of D,L-3-formyl-2,2-pentamethylene-5,5-dimethyl-thiazolidine-4-carboxylic acid and 15.1 grams (0.1 mole) of 1-norephedrine as starting materials. The recovered salt of D-3-formyl-2,2-pentamethylene-5,5-dimethyl-thiazolidine-4-carboxylic acid and 1-norephedrine had a specific rotation of +25° and a melting point of 190°–191°C. The yield amounted to 31 grams, corresponding to 76%. The salt was split as described in Example 1. THe D-3-formyl-2,2-pentamethylene-5,5-dimethyl-thiazolidine-4-carboxylic acid thereby recovered had a specific rotation of +62.2° and a melting point of 191°–192°C. From this there were obtained by splitting in the manner described in Example 1 nine grams of D-penicillamine having a melting point of 202°–205°C. and a specific rotation of −62.5°.

What is claimed is:

1. A process comprising the step of crystallizing out of solution the salt of an optically active base with an optically active form of penicillamine having at least one of the hydrogen atoms of the mercapto group and the amino group protected as a compound of the formula:

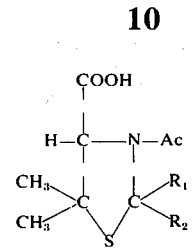

where $R_1$ and $R_2$ are both methyl or $R_1$ and $R_2$ are joined together to form the pentamethylene group and Ac is formyl employing the D,L racemate form of said protected penicillamine and 1-norephedrine free of d-norephedrine and precipitating the salt of the D-form of the protected penicillamine and the 1-norephedrine.

2. A process according to claim 1 wherein the solvent is water, alcohol, aliphatic hydrocarbon, halogenated aliphatic hydrocarbon, dioxane, a ketone, an ester or an aromatic hydrocarbon.

3. A process according to claim 1, wherein $R_1$ and $R_2$ are both methyl.

4. A process according to claim 3, wherein there are used 0.1 to 3 moles of 1-norephedrine per mole of racemate.

5. A process according to claim 4 wherein there are used 0.5 to 1.1 mole of the 1-norephedrine.

6. A process according to claim 1, wherein $R_1$ and $R_2$ are joined together to form the pentamethylene group.

7. A process according to claim 6, wherein there are used 0.1 to 3 moles of 1-norephedrine per mole of racemate.

8. A process according to claim 7 wherein there are used 0.5 to 1.1 moles of the 1-norephedrine.

9. A process according to claim 1 wherein $R_1$ and $R_2$ are both methyl, there are used 0.1 to 3 moles of 1-norephedrine per mole of racemate and the solvent is ethyl acetate, isopropyl alcohol, toluene, acetone, dioxane, benzene or carbon tetrachloride.

10. A process comprising the step of crystallizing out of solution the salt of an optically active base with an optically active form of penicillamine having at least one of the hydrogen atoms of the mercapto group and the amino group protected as a compound of the formula:

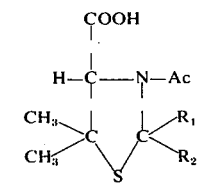

in which $R_1$ and $R_2$ are both methyl or $R_1$ and $R_2$ are joined together to form the pentamethylene group and Ac is formyl, employing the D,L racemate form of said protected penicillamine and a salt of 1-norephedrine free of d-norephedrine and precipitating the salt of the D-form of the protected penicillamine and 1-norephedrine.

11. A process according to claim 10 wherein the salt of 1-norephedrine is a salt of an organic acid.

12. A process according to claim 11 wherein the salt of 1-norephedrine is a salt of a sulfonic acid or a carboxylic acid.

13. A process according to claim 12 wherein the acid is unsubstituted or is substituted by hydroxy, —OR, —SH, —SR, halogen, —NH₂, —NHR or

where R is alkyl.

14. A process according to claim 13 wherein the acid is unsubstituted or is substituted by hydroxy, —OR, —SH, —SR, or halogen.

15. A process according to claim 14 wherein the acid is unsubstituted or substituted with —OH.

16. A process according to claim 15 wherein the acid is unsubstituted.

17. A process according to claim 16 wherein the acid is an alkanoic acid, phenylalkanoic acid, alkenoic acid, phenylalkenoic acid, hydroxyalkanoic acid, phenylhydroxyalkanoic acid, hydroxyaryl carboxylic acid, aryl carboxylic acid or heterocyclic carboxylic acid.

18. A process according to claim 17 wherein the acid has 1 to 3 carboxylic acid groups.

19. A process according to claim 18 wherein the alkanoic acid had 1 to 6 carbon atoms, the hydroxylakanoic acid has 2 to 6 carbon atoms, the phenylalkanoic acid has 2 to 3 carbon atoms in the alkanoic acid portion of the molecule, the alkenoic acid has 3 to 4 carbon atoms, the phenylalkenoic acid has 3 carbon atoms in the alkenoic acid portion of the molecule, the phenylhydroxyalkanoic acid has 3 carbon atoms in the hydroxyalkanoic acid portion of the the molecule, the aryl carboxylic acid is a benzene mono or dicarboxylic acid, the hydroxyaryl carboxylic acid is hydroxybenzoic acid and the heterocyclic carboxylic acid has the carboxylic group attached to a carbon atom of the heterocyclic ring, the heterocyclic ring containing 5 to 6 carbon atoms, said heterocyclic ring having 1 to 2 hetero atoms, the hetero atoms being selected from the group consisting of oxygen, nitrogen and sulfur, the carboxyl group being the sole substituent on the ring.

20. A process according to claim 19 wherein the acid is formic acid, acetic acid or propionic acid.

21. A process according to claim 20 wherein the acid is benzene sulfonic acid or toluene sulfonic acid.

22. A process according to claim 18, wherein R₁ and R₂ are both methyl.

23. A process according to claim 18, wherein R₁ and R₂ are joined together and are pentamethylene.

24. A process according to claim 10 wherein the salt is the salt of an alkanoic acid, phenylalkanoic acid, alkenoic acid, phenylalkenoic acid, hydroxyalkanoic acid, phenylhydroxyalkanoic acid, hydroxyaryl carboxylic acid, aryl carboxylic acid, alkane sulfonic acid, arylsulfonic acid or heterocyclic carboxylic acid where the heterocyclic group is the thiophene, thiazole, furan or pyridine or indole group.

25. A process according to claim 24 wherein the salt is the 1-norephedrine salt of acetic acid, propionic acid, maleic acid, benzoic acid, formic acid, phenylpropionic acid, citric acid or benzenesulfonic acid.

26. A process according to claim 10 wherein the salt is a salt of an alkanoic acid, phenylalkanoic acid, alkenoic acid, phenylalkenoic acid, hydroxyalkanoic acid, phenylhydroxyalkanoic acid, hydroxyaryl carboxylic acid, aryl carboxylic acid, alkanesulfonic acid, arylsulfonic acid, sulfuric acid, hydrochloric acid, hydrobromic acid, nitric acid or phosphoric acid.

27. A process according to claim 10 wherein the salt is a salt of isobutyric acid, n-valeric acid, isovaleric acid, trimethylacetic acid, lactic acid, oxalic acid, malonic acid, adipic acid, maleic acid, succinic acid, tartaric acid, citric acid, formic acid, acetic acid, propionic acid, phenylacetic acid, mandelic acid, cinnamic acid, 3-phenyl propionic acid, phthalic acid, terephthalic acid, salicylic acid, benzoic acid, thiophene-2-carboxylic acid, thiazole-4-carboxylic acid, furane-2-carboxylic acid picolinic acid, isonictinic acid, methanesulfonic acid, methane trisulfonic acid, propane-2-sulfonic acid, p-toluenesulfonic acid or benzene sulfonic acid.

* * * * *

UNITED STATES PATENT OFFICE
CERTIFICATE OF CORRECTION

Patent No. 3,966,752          Dated June 29, 1976

Inventor(s) Friedrich Asinger, Heribert Offermanns, Karl-Heinz Gluzek and Walter von Bebenburg It is certified that error appears in the above-identified patent and that said Letters Patent are hereby corrected as shown below:

[30]   July 30, 1971      Germany           2138122

November 29, 1972  Germany           2258411

Signed and Sealed this

Second Day of November 1976

[SEAL]

*Attest:*

RUTH C. MASON
*Attesting Officer*

C. MARSHALL DANN
*Commissioner of Patents and Trademarks*